US007666655B2

(12) United States Patent
Vitushkina et al.

(10) Patent No.: US 7,666,655 B2
(45) Date of Patent: Feb. 23, 2010

(54) *ESCHERICHIA* BACTERIA TRANSFORMED WITH THE YDDG GENE TO ENHANCE L-AMINO ACID PRODUCING ACTIVITY

(75) Inventors: Maria Viacheslavovna Vitushkina, Moscow (RU); Vitaliy Arkadyevich Livshits, Moscow (RU); Sergei Vladimirovich Mashko, Moscow (RU); Vera Georgievna Doroshenko, Moscow (RU); Irina Vladimirovna Biryukova, Moscow (RU); Zhanna Iosifovna Katashkina, Moscow (RU); Aleksandra Yurievna Skorokhodova, Moscow (RU); Alla Valentinovna Belareva, Moscow (RU)

(73) Assignee: Ajinomoto Co., Inc., Tokyo (JP)

( * ) Notice: Subject to any disclaimer, the term of this patent is extended or adjusted under 35 U.S.C. 154(b) by 202 days.

(21) Appl. No.: 10/302,997

(22) Filed: Nov. 25, 2002

(65) Prior Publication Data

US 2003/0157667 A1 Aug. 21, 2003

(30) Foreign Application Priority Data

Nov. 23, 2001 (RU) ............................... 2001131571
Aug. 14, 2002 (RU) ............................... 2002121670

(51) Int. Cl.
*C12N 1/20* (2006.01)
*C12N 1/21* (2006.01)
(52) U.S. Cl. .............................. 435/252.3; 435/252.33; 435/320.1; 435/6; 435/69.1
(58) Field of Classification Search ............ 435/252.33, 435/320.1, 106, 108; 536/23.7
See application file for complete search history.

(56) References Cited

U.S. PATENT DOCUMENTS

| 3,786,039 | A | 1/1974 | Ariyoshi et al. | |
|---|---|---|---|---|
| 4,278,765 | A | 7/1981 | Debabov et al. | |
| 4,783,403 | A | 11/1988 | Araki et al. | |
| 5,972,663 | A | 10/1999 | Winterhalter et al. | |
| 6,316,232 | B1 | 11/2001 | Sprenger et al. | |
| 7,259,003 | B2 * | 8/2007 | Livshits et al. | ......... 435/252.33 |
| 2005/0239177 | A1 | 10/2005 | Livshits et al. | |

FOREIGN PATENT DOCUMENTS

| EP | 0 488 424 A2 | 6/1992 |
|---|---|---|
| EP | 0 877 090 A1 | 11/1998 |
| EP | 0 994 190 | 4/2000 |
| EP | 1 016 710 | 7/2000 |
| JP | 2000-189177 | 7/2000 |
| SU | 1694643 | 11/1987 |
| SU | 974817 | 8/1990 |
| WO | WO 97/23597 | 7/1997 |
| WO | WO 02/077183 A2 | 10/2002 |

OTHER PUBLICATIONS

Blattner et al., The Complete Genome Sequence of *Escherichia coli* K-12, Sep. 1997, Science, vol. 277, pp. 1453-1462.*
T. Dassler, et al., Molecular Microbiology, vol. 36, No. 5, pp. 1101-1112, "Identification of a Major Facilitator Protein From *Escherichia coli* Involved in Efflux of Metabolites of the Cysteine Pathway", 2000.
L. Gold, et al., Ann. Rev. Microbiol., vol. 35, pp. 365-403, "Translational Initiation in Prokaryotes", 1981.
A. Hui, et al., The EMBO Journal, vol. 3, No. 3, pp. 623-629, "Mutagenesis of the Three Bases Preceding the Start Codon of the β-Galactosidase mRNA and Its Effect on Translation in *Escherichia coli*", 1984.
O. B. Astaurova, et al., Applied Biochemistry and Microbiology, vol. 27, No. 5, pp. 556-561, "Comparative Study of Amino-Acid-Producing *E. coli* Strains", Sep.-Oct. 1991.
O. B. Astaurova, et al., Applied Biochemistry and Microbiology, vol. 21, No. 5, pp. 485-490, "Animation in Strains of *Escherichia coli* Which Effectively Synthesize Threonine", Sep.-Oct. 1985.
A. Y. Chistoserdov, et al., Plasmid, vol. 16, pp. 161-167, "Broad Host Range Vectors Derived From an RSF1010::Tn1 Plasmid", 1986.
H. Giladi, et al., J. Mol. Biol., vol. 260, pp. 484-491, "Identification of an UP Element Within the IHF Binding Site at the $P_L1$-$P_L2$ Tandem Promoter of Bacteriophage λ", 1996.
K. A. Datsenko, et al., PNAS, vol. 97, No. 12, pp. 6640-6645, "One-Step Inactivation of Chromosomal Genes in *Escherichia coli* K-12 Using PCR Products", Jun. 6, 2000.
U. Deuschle, et al., The EMBO Journa.l, vol. 5, No. 11, pp. 2987-2994, "Promoters of *Eschirichia coli*: A Hierarchy of in Vivo Strength Indicates Alternate Structures", 1986.
M. M. Gusyatiner, et al., Genetika (Genetics), vol. XIV, No. 6, pp. 957-968, "Investigation of the relA Gene Function in the Expression of Amino Acid Operons", Jun. 1978 (with English translation).
Database EMBL Online, Dec. 21, 1996, "*E. coli* Genomic DNA, Kohara Clone #277 (33.2-33.6 Min.)", XP-002321437, Database accession No. ECD788.
Database UniProt Online, Nov. 1, 1995, "Hypothetical Protein YDDG.", XP-002321438, Database accession No. YDDG_ECOLI.
Database Geneseq Online, Jun. 19, 2003, "Prokaryotic Essential Gene #837.", XP-002321439, Database accession No. ACA19180. (corresponds to WO 02/077183 A2).

(Continued)

*Primary Examiner*—Hope A Robinson
(74) *Attorney, Agent, or Firm*—Oblon, Spivak, McClelland, Maier & Neustadt, L.L.P.

(57) ABSTRACT

The present invention relates to a method for producing L-amino acid, such as L-phenylalanine and L-tryptophan, is provided using bacterium belonging to the genus *Escherichia* wherein the L-amino acid productivity of said bacterium is enhanced by enhancing an activity of protein encoded by the yddG gene from *Escherichia coli*, wherein said protein has an activity to make said bacterium resistant to L-phenylalanine, a phenylalanine analogue, or a tryptophan analogue. The present invention further relates to a method for producing lower alkyl ester of α-L-aspartyl-L-phenylalanine.

26 Claims, 1 Drawing Sheet

OTHER PUBLICATIONS

Database UniProt Online, Mar. 1, 2002, "Hypothetical Protein YDDG (Hypothetical Protein ECS2077).", XP-002321440, Database accession No. Q8XAS1.

H. Aiba, et al., "A 570-KB DNA Sequence of the *Escherichia coli* K-12 Genome Corresponding to the 28.0-40.1 Min Region on the Linkage Map", DNA Research 3, 1996, pp. 363-377.

N.P. Zakataeva, et al., Abstracts pf 17th International Congress of Biochemistry and Molecular Biology in conjunction with 1997 Annual Meeting of the American Society for Biochemistry and Molecular Biology, Abstract No. 457, Aug. 24-29, 1997.

GenBank Accession No. AE000287 U00096, Dec. 1, 2000.

GenBank Accession No. NC_000913, Dec. 9, 2002.

GenBank Accession No. NP_415990, Dec. 9, 2002.

Frederick R. Blattner, et al., "The Complete Genome Sequence of *Escherichia coli* K-12", Science, Sep. 5, 1997, vol. 277, pp. 1453-1474.

* cited by examiner

SEQUENCE LISTING

```
<160> NUMBER OF SEQ ID NOS: 15

<210> SEQ ID NO 1
<211> LENGTH: 882
<212> TYPE: DNA
<213> ORGANISM: Escherichia coli

<400> SEQUENCE: 1
atgacacgac aaaaagcaac gctcataggg ctgatagcga tcgtcctgtg gagcacgatg     60
gtaggattga ttcgcggtgt cagtgagggg ctcggcccgg tcggcggcgc agctgctatc    120
tattcattaa gcgggctgct gttaatcttc acggttggat ttccgcgtat tcggcaaatc    180
ccgaaaggct atttactcgc cgggagtctg ttattcgtca gctatgaaat ctgtctggcg    240
ctttccttag ggtatgcggc gacccatcat caggcgattg aagtgggtat ggtgaactat    300
ctgtggccca gcctgacaat tctctttgcc attctgttta atggtcagaa aaccaactgg    360
ttgattgtac ctggattatt attagccctc gtcggcgtct gttgggtgtt aggcggtgac    420
aatgggttac attatgatga aatcatcaat aatatcacca ccagcccatt gagttatttc    480
ctggcgttca ttggtgcgtt tatctgggca gcctattgca cagtaacgaa taaatacgca    540
cgcggattta atggaattac cgttttttgtc ctgctaacgg gagcaagtct gtgggtttac    600
tattttctta cgccacaacc agaaatgata tttagcacgc ccgtcatgat taaactcatc    660
tctgcggcat ttaccttagg atttgcttat gctgcatgga atgtcggtat attgcatggc    720
aatgtcacca ttatggcggt aggttcgtat tttacgcctg tactttcctc agcgcttgca    780
gccgtgctgc tcagcgcccc gctgtcgttc tcgttctggc aaggcgcgct gatggtctgc    840
ggcggttccc tgctctgctg gctggcgaca cgtcgtggtt aa                       882
```

```
<210> SEQ ID NO 2
<211> LENGTH: 293
<212> TYPE: PRT
<213> ORGANISM: Escherichia coli

<400> SEQUENCE: 2

Met Thr Arg Gln Lys Ala Thr Leu Ile Gly Leu Ile Ala Ile Val Leu
 1               5                  10                  15

Trp Ser Thr Met Val Gly Leu Ile Arg Gly Val Ser Glu Gly Leu Gly
                20                  25                  30

Pro Val Gly Gly Ala Ala Ile Tyr Ser Leu Ser Gly Leu Leu Leu
            35                  40                  45

Ile Phe Thr Val Gly Phe Pro Arg Ile Arg Gln Ile Pro Lys Gly Tyr
        50                  55                  60

Leu Leu Ala Gly Ser Leu Leu Phe Val Ser Tyr Glu Ile Cys Leu Ala
 65                 70                  75                  80

Leu Ser Leu Gly Tyr Ala Ala Thr His His Gln Ala Ile Glu Val Gly
                85                  90                  95

Met Val Asn Tyr Leu Trp Pro Ser Leu Thr Ile Leu Phe Ala Ile Leu
            100                 105                 110

Phe Asn Gly Gln Lys Thr Asn Trp Leu Ile Val Pro Gly Leu Leu Leu
        115                 120                 125

Ala Leu Val Gly Val Cys Trp Val Leu Gly Gly Asp Asn Gly Leu His
    130                 135                 140

Tyr Asp Glu Ile Ile Asn Asn Ile Thr Thr Ser Pro Leu Ser Tyr Phe
145                 150                 155                 160

Leu Ala Phe Ile Gly Ala Phe Ile Trp Ala Ala Tyr Cys Thr Val Thr
                165                 170                 175

Asn Lys Tyr Ala Arg Gly Phe Asn Gly Ile Thr Val Phe Val Leu Leu
            180                 185                 190

Thr Gly Ala Ser Leu Trp Val Tyr Tyr Phe Leu Thr Pro Gln Pro Glu
        195                 200                 205

Met Ile Phe Ser Thr Pro Val Met Ile Lys Leu Ile Ser Ala Ala Phe
    210                 215                 220

Thr Leu Gly Phe Ala Tyr Ala Ala Trp Asn Val Gly Ile Leu His Gly
225                 230                 235                 240

Asn Val Thr Ile Met Ala Val Gly Ser Tyr Phe Thr Pro Val Leu Ser
                245                 250                 255

Ser Ala Leu Ala Ala Val Leu Leu Ser Ala Pro Leu Ser Phe Ser Phe
            260                 265                 270

Trp Gln Gly Ala Leu Met Val Cys Gly Gly Ser Leu Leu Cys Trp Leu
        275                 280                 285

Ala Thr Arg Arg Gly
    290

<210> SEQ ID NO 3
<211> LENGTH: 25
<212> TYPE: DNA
<213> ORGANISM: Artificial Sequence
<220> FEATURE:
<223> OTHER INFORMATION: Synthetic DNA

<400> SEQUENCE: 3
tgatcggatc cgaaatgaga tataa                                       25

<210> SEQ ID NO 4
```

```
<211> LENGTH: 24
<212> TYPE: DNA
<213> ORGANISM: Artificial Sequence
<220> FEATURE:
<223> OTHER INFORMATION: Synthetic DNA

<400> SEQUENCE: 4
ctgcggtcga cgtccattgc tttc                                            24

<210> SEQ ID NO 5
<211> LENGTH: 29
<212> TYPE: DNA
<213> ORGANISM: Artificial Sequence
<220> FEATURE:
<223> OTHER INFORMATION: Synthetic DNA

<400> SEQUENCE: 5
gaccatagat ctgaattcga gctcggtac                                       29

<210> SEQ ID NO 6
<211> LENGTH: 29
<212> TYPE: DNA
<213> ORGANISM: Artificial Sequence
<220> FEATURE:
<223> OTHER INFORMATION: Synthetic DNA

<400> SEQUENCE: 6
acggccagat ctaagcttgc atgcctgca                                       29

<210> SEQ ID NO 7
<211> LENGTH: 34
<212> TYPE: DNA
<213> ORGANISM: Artificial Sequence
<220> FEATURE:
<223> OTHER INFORMATION: Synthetic DNA

<400> SEQUENCE: 7
aacagtgatc atttgcctgg cggcagtagc gcgg                                 34

<210> SEQ ID NO 8
<211> LENGTH: 41
<212> TYPE: DNA
<213> ORGANISM: Artificial Sequence
<220> FEATURE:
<223> OTHER INFORMATION: Synthetic DNA

<400> SEQUENCE: 8
ataaaaagct tagatctcaa aaagagtttg tagaaacgca a                         41

<210> SEQ ID NO 9
<211> LENGTH: 160
<212> TYPE: DNA
<213> ORGANISM: Escherichia coli

<400> SEQUENCE: 9
cgccttcgca aattgaccta cctcaatagc ggtagaaaaa cgcaccactg cctgacaggc     60
cagttaaaaa aatgctataa aattcagctt aattttaac ggcaagagag acaaaacagc    120
gagcatgaca cgacaaaaag caacgctcat agggctgata                         160

<210> SEQ ID NO 10
<211> LENGTH: 29
<212> TYPE: DNA
<213> ORGANISM: Artificial Sequence
<220> FEATURE:
<223> OTHER INFORMATION: Synthetic DNA
```

<400> SEQUENCE: 10
aaatcagatc ttcagaattc tcacctacc                                    29

<210> SEQ ID NO 11
<211> LENGTH: 69
<212> TYPE: DNA
<213> ORGANISM: Artificial Sequence
<220> FEATURE:
<223> OTHER INFORMATION: Synthetic DNA

<400> SEQUENCE: 11
tatcagccct atgagcgttg cttttgtcg tgtcatagct gtttccttct agacggccaa   60
tgcttcgta                                                          69

<210> SEQ ID NO 12
<211> LENGTH: 34
<212> TYPE: DNA
<213> ORGANISM: Artificial Sequence
<220> FEATURE:
<223> OTHER INFORMATION: Synthetic DNA

<400> SEQUENCE: 12
tagcgaagat ctctgatgtc cggcggtgct tttg                              34

<210> SEQ ID NO 13
<211> LENGTH: 57
<212> TYPE: DNA
<213> ORGANISM: Artificial Sequence
<220> FEATURE:
<223> OTHER INFORMATION: Synthetic DNA

<400> SEQUENCE: 13
cgccttcgca aattgaccta cctcaatagc ggtagattac gccccgccct gccactc     57

<210> SEQ ID NO 14
<211> LENGTH: 1362
<212> TYPE: DNA
<213> ORGANISM: Artificial Sequence
<220> FEATURE:
<223> OTHER INFORMATION: Synthetic DNA

<400> SEQUENCE: 14
cgccttcgca aattgaccta cctcaatagc ggtagattac gccccgccct gccactcatc   60
gcagtactgt tgtaattcat taagcattct gccgacatgg aagccatcac agacggcatg  120
atgaacctga atcgccagcg gcatcagcac cttgtcgcct tgcgtataat atttgcccat  180
ggtgaaaacg ggggcgaaga agttgtccat attggccacg tttaaatcaa aactggtgaa  240
actcacccag ggattggctg agacgaaaaa catattctca ataaacccctt tagggaaata  300 ggccaggttt tcaccgtaac acgccacatc ttgcgaatat atgtgtagaa actgccggaa  360
atcgtcgtgg tattcactcc agagcgatga aaacgtttca gtttgctcat ggaaaacggt  420
gtaacaaggg tgaacactat cccatatcac cagctcaccg tctttcattg ccatacggaa  480
ttccggatga gcattcatca ggcgggcaag aatgtgaata aaggccggat aaaacttgtg  540
cttatttttc tttacggtct ttaaaaaggc cgtaatatcc agctgaacgg tctggttata  600
ggtacattga gcaactgact gaaatgcctc aaaatgttct ttacgatgcc attgggatat  660
atcaacggtg gtatatccag tgatttttt ctccatttta gcttccttag ctcctgaaaa  720
tctcgataac tcaaaaaata cgcccggtag tgatcttatt tcattatggt gaaagttgga  780

```
acctcttacg tgccgatcaa cgtctcattt tcgccaaaag ttggcccagg gcttcccggt      840
atcaacaggg acaccaggat ttatttattc tgcgaagtga tcttccgtca caggtattta      900
ttcggcgcaa agtgcgtcgg gtgatgctgc caacttactg atttagtgta tgatggtgtt      960
tttgaggtgc tccagtggct tctgtttcta tcagctgtcc ctcctgttca gctactgacg     1020
gggtggtgcg taacggcaaa agcaccgccg gacatcagag atcttcacct accaaacaat     1080 gccccctgc aaaaaataaa ttcatataaa aaacatacag ataaccatct gcggtgataa      1140
attatctctg gcggtgttga cataaatacc actggcggtg atactgagca catcagcagg     1200
acgcactgac caccatgaag gtgacgctct taaaaattaa gccctgaaga agggcagcat     1260
tcaaagcaga aggctttggg gtgtgtgata cgaaacgaag cattggccgt ctagaaggaa     1320
acagctatga cacgacaaaa agcaacgctc atagggctga ta                       1362
```

```
<210> SEQ ID NO 15
<211> LENGTH: 17
<212> TYPE: DNA
<213> ORGANISM: Artificial Sequence
<220> FEATURE:
<223> OTHER INFORMATION: Synthetic DNA

<400> SEQUENCE: 15
ttaaccacga cgtgtcg                                                      17
```

ESCHERICHIA BACTERIA TRANSFORMED WITH THE YDDG GENE TO ENHANCE L-AMINO ACID PRODUCING ACTIVITY

TECHNICAL FIELD

The present invention relates to biotechnology, specifically to a method for producing amino acids, namely aromatic acids, such as L-phenylalanine and L-tryptophan, by fermentation, and more specifically to a gene derived from bacterium *Escherichia coli*. The gene is useful for improvement of L-phenylalanine and L-tryptophan productivity.

BACKGROUND ART

Conventionally the L-amino acids have been industrially produced by method of fermentation utilizing strains of microorganisms obtained from natural sources or mutants of the same especially modified to enhance L-amino acid productivity.

There have been disclosed many techniques to enhance L-amino acid productivity, for example, by transformation of microorganism by recombinant DNA (see, for example, U.S. Pat. No. 4,278,765). These techniques are based on the increasing of activities of the enzymes involved in amino acid biosynthesis and/or desensitizing the target enzymes from the feedback inhibition by produced L-amino acid (see, for example, Japanese Laid-open application No56-18596 (1981), WO 95/16042 or U.S. Pat. Nos. 5,661,012 and 6,040, 160).

On the other hand, the enhancement of amino acid excretion activity may improve the productivity of L-amino acid producing strain. Lysine-producing strain of a bacterium belonging to the genus *Corynebacterium* having increased expression of L-lysine excretion gene (lysE gene) is disclosed (WO 9723597A2). In addition, genes encoding efflux proteins suitable for secretion of L-cysteine, L-cystine, N-acetylserine or thiazolidine derivatives are also disclosed (U.S. Pat. No. 5,972,663).

At present, several *Escherichia coli* genes encoding putative membrane proteins enhancing L-amino acid production are disclosed. Additional copies of rhtB gene make a bacterium more resistant to L-homoserine and enhance the production of L-homoserine, L-threonine, L-alanine, L-valine and L-isoleucine (European patent application EP994190A2). Additional copies of the rhtC gene make a bacterium more resistant to L-homoserine and L-threonine and enhance production of L-homoserine, L-threonine and L-leucine (European patent application EP1013765A1). Additional copies of yahN, yeaS, yfiK and yggA genes enhance production of L-glutamic acid, L-lysine, L-threonine, L-alanine, L-histidine, L-proline, L-arginine, L-valine and L-isoleucine (European patent application EP1016710A2).

Earlier the present inventors obtained, with respect to *E.coli* K-12, a mutant having a mutation, thrR (herein referred to as rhtA23) that is concerned in resistance to high concentrations of threonine or homoserine in a minimal medium (Astaurova, O. B. et al., *Appl. Bioch. and Microbiol.*, 21, 611-616 (1985)). The mutation improved the production of L-threonine (SU Patent No.974817), homoserine and glutamate (Astaurova, O. B. et al., *Appl. Bioch. and Microbiol.*, 27, 556-561, 1991) by the respective *E. coli* producing strains.

Furthermore, the present inventors have revealed that the rhtA gene exists at 18 min on *E.coli* chromosome close to the glnHPQ operon that encodes components of the glutamine transport system, and that the rhtA gene is identical to ybiF ORF between pexB and ompX genes. The unit expressing a protein encoded by the ORF has been designated as rhtA (rht: resistance to homoserine and threonine) gene.

Besides, the present inventors have found that the rhtA gene amplification also conferred resistance to homoserine and threonine. The rhtA23 mutation is an A-for-G substitution at position −1 with respect to the ATG start codon (ABSTRACTS of 17th International Congress of Biochemistry and Molecular Biology in conjugation with 1997 Annual Meeting of the American Society for Biochemistry and Molecular Biology, San Francisco, Calif. Aug. 24-29, 1997, abstract No. 457). It is known that the nucleotide composition of the spacer between the SD sequence and start codon and especially the sequences immediately upstream of the start codon profoundly affect mRNA translatability. A 20-fold range in the expression levels was found, depending on the nature of the three nucleotides preceding the start codon (Gold et al., Annu. Rev. Microbiol., 35, 365-403, 1981; Hui et al., EMBO J., 3, 623-629, 1984). Therefore, it may be predicted that rhtA23 mutation increases expression of rhtA gene.

The rhtA gene encodes a protein that consists of 295 amino acid residues and has calculated molecular weight of 31.3 kDa. The analysis of the RhtA sequence revealed that it is a highly hydrophobic protein containing 10 predicted transmembrane segments. A PSI-BLAST search of the nucleotide sequence of *E.coli* strain K-12 belonging to the genus *Escherichia* (Science, 277, 1453-1474 (1997)) revealed at least 10 proteins homologous to RhtA. Among them there are proteins encoded by ydeD and yddG genes. It was shown the ydeD gene is involved into efflux of the cysteine pathway metabolites (Daβler et al., Mol. Microbiol., 36, 1101-1112, 2000; U.S. Pat. No. 5,972,663). The yddG gene has been known as putative CDS, which may encode functionally unknown protein (numbers 3687 to 4568 in the sequence of GenBank accession AE000244 U00096).

DISCLOSURE OF THE INVENTION

An object of present invention is to enhance the productivity of L-phenylalanine producing strain and to provide a method for producing L-phenylalanine using the strain. Also an object of present invention is to enhance the productivity of L-tryptophan producing strain and to provide a method for producing L-tryptophan using the strain.

This aim was achieved by identifying the yddG gene encoding a membrane protein, homologue to RhtA, which is not involved in biosynthetic pathway of target L-amino acid, conferred on a microorganism resistance to phenylalanine and several amino acid analogues when the wild type allele of the gene was amplified on a multi copy vector in the microorganism. Besides, the yddG gene can enhance L-phenylalanine production when its additional copies are introduced into the cells of the respective producing strain. And the yddG gene can enhance L-tryptophan production when its expression in the cells of the respective producing strain is enhanced. Thus the present invention has been completed.

The present inventions are as follows:

1) An L-amino acid producing bacterium belonging to the genus *Escherichia*, wherein the L-amino acid production by the bacterium is enhanced by enhancing an activity of a protein as defined in the following (A) or (B) in a cell of the bacterium:

(A) a protein which comprises the amino acid sequence shown in SEQ ID NO: 2 in Sequence listing;

(B) a protein which comprises an amino acid sequence including deletion, substitution, insertion or addition of one or several amino acids in the amino acid sequence shown in SEQ ID NO: 2 in Sequence listing, and which has an activity of making bacterium having enhanced resistance to L-phenylalanine and/or an amino acid analog such as p-fluoro-phenylalanine and 5-fluoro-DL-tryptophane or the like;

(hereinafter, the proteins as defined in the above (A) or (B) are referred to as "proteins of the present invention")

2) The bacterium according to the above bacterium, wherein the activity of the protein as defined in (A) or (B) is enhanced by transformation of the bacterium with a DNA coding for the protein as defined in (A) or (B), or by alteration of expression regulation sequence of said DNA on the chromosome of the bacterium.

3) The bacterium according to the above bacterium, wherein the transformation is performed with a multicopy vector containing the DNA.

4) The bacterium according to the above bacterium, wherein native promoter of said DNA is substituted with more potent promoter.

5) A method for producing an L-amino acid; which comprises cultivating the bacterium according to the above bacterium in a culture medium and collecting from the culture medium the L-amino acid to be produced and accumulated in the medium.

6) The method according to the above method, wherein the L-amino acid is L-phenylalanine.

7) The method according to the above method, wherein the bacterium has enhanced expression of genes for phenylalanine biosynthesis.

8) The method according to the above method, wherein the L-amino acid is L-tryptophan.

9) The method according to the above method, wherein the bacterium has enhanced expression of genes for tryptophan biosynthesis.

10) A method for producing lower alkyl ester of α-L-aspartyl-L-phenylalanine, comprising cultivating the bacterium according the above acterium in a culture medium to produce and accumulate L-phenylalanine in the medium, said bacterium having L-phenylalanine productivity, and synthesizing lower alkyl ester of α-L-aspartyl-L-phenylalanine from aspartic acid or its derivative and the obtained L-phenylalanine.

11) The method according to claim 10, further comprising esterifying L-phenylalanine to generate a lower alkyl ester of L-phenylalanine, condensing the lower alkyl ester of L-phenylalanine with the aspartic acid derivative, wherein the derivative is N-acyl-L-aspartic anhydride, separating the lower alkyl ester of N-acyl-α-L-aspartyl-L-phenylalanine from the reaction mixture, and hydrogenating the lower alkyl ester of N-acyl-α-L-aspartyl-L-phenylalanine to generate the lower alkyl ester of α-L-aspartyl-L-phenylalanine.

In the present invention, an amino acid is of L-configuration unless otherwise noted.

The method for producing L-amino acid includes production of L-phenylalanine using L-phenylalanine producing bacterium wherein activities of the proteins of the present invention such as that comprising amino acid sequence shown in SEQ ID NO: 2 are enhanced. In addition, the method for producing L-amino acid includes production of L-tryptophan using L-tryptophan producing bacterium wherein activities of the proteins of the present invention such as that comprising amino acid sequence shown in SEQ ID NO: 2 are enhanced.

The present invention will be explained in detail below.

The bacterium of the present invention is an L-amino acid producing bacterium belonging to the genus *Escherichia*, wherein the L-amino acid production by the bacterium is enhanced by enhancing an activity of the protein of the present invention in a cell of the bacterium.

In the present invention, "L-amino acid producing bacterium" means a bacterium which has an ability to produce and accumulate the L-amino acid in a medium, when the bacterium is cultured in the medium. The L-amino acid producing ability may be possessed by the bacterium as a property of a wild strain of the bacterium or may be imparted or enhanced by breeding.

Preferred embodiment of the bacterium of present invention is L-phenylalanine producing bacterium belonging to the genus *Escherichia* that has enhanced activity of the proteins of the present invention. More concretely, the bacterium of the present invention harbors the DNA having yddG gene overexpressed in the chromosome or in a plasmid in the bacterium and has enhanced ability to produce L-phenylalanine. Another preferred embodiment of the bacterium of the present invention is L-tryptophan producing bacterium belonging to the genus *Escherichia* that has enhanced activity of the proteins of the present invention. More concretely, the bacterium of the present invention harbors the DNA having yddG gene overexpressed in the chromosome or in a plasmid in the bacterium and has enhanced ability to produce L-tryptophan.

The protein of the present invention includes those as defined in the following, (A) or (B):

(A) a protein which comprises the amino acid sequence shown in SEQ ID NO: 2 in Sequence listing;

(B) a protein which comprises an amino acid sequence including deletion, substitution, insertion or addition of one or several amino acids in the amino acid sequence shown in SEQ ID NO: 2 in Sequence listing, and which has an activity of making bacterium having enhanced resistance to an amino acid such as phenylalanine and/or an amino acid analog such as p-fluoro-phenylalanine, 5-fluoro-DL-tryptophane or the like.

The number of "several" amino acids differs depending on the position or the type of amino acid residues in the three-dimensional structure of the protein. It may be 2 to 30, preferably 2 to 15, and more preferably 2 to 5 for the protein ((A).

"Resistance to L-phenylalanine and/or an amino acid analog" means ability for bacterium to grow on a minimal medium containing L-phenylalanine or the amino acid analog in concentration under which unmodified or the wild type, or the parental strain of the bacterium cannot grow, or ability for bacterium to grow faster on a medium containing L-phenylalanine or the amino acid analog than unmodified or the wild type, or the parental strain of the bacterium. L-amino acid analogs are exemplified by p-fluoro-phenylalanine, 5-fluoro-DL-tryptophane or the like. Above mentioned concentration of L-amino acid is generally 10 to 25 mg/ml, preferably 15 to 20 mg/ml in case of L-phenylalanine. Above mentioned concentration of amino acid analog is generally 0.1 to 5 mg/ml, preferably 0.5 to 2.0 mg/ml in case of p-fluoro-phenylalanine, and generally 0.2 to 20 μg/ml, preferably 2 to 5 μg/ml in case of 5-fluoro-DL-tryptophane.

The bacterium of the present invention also includes one wherein the activity of the protein of the present invention is enhanced by transformation of said bacterium with DNA coding for protein as defined in (A) or (B), or by alteration of expression regulation sequence of said DNA on the chromosome of the bacterium.

The DNA, which is used for modification of the bacterium of the present invention may code for a protein having L-amino acid excretion activity. More concretely, the DNA is represented by yddG gene. The yddG gene can be obtained by, for example, PCR using primers based on the nucleotide sequence shown in SEQ ID No: 1.

The DNA of the present invention includes a DNA coding for the protein which include deletion, substitution, insertion or addition of one or several amino acids in one or more positions on the protein (A) as long as they do not lose the activity of the protein. Although the number of "several" amino acids differs depending on the position or the type of amino acid residues in the three-dimensional structure of the protein, it may be 2 to 30, preferably 2 to 15, and more preferably 2 to 5 for the protein (A). The DNA coding for substantially the same protein as the protein defined in (A) may be obtained by, for example, modification of nucleotide sequence coding for the protein defined in (A) using site-directed mutagenesis so that one or more amino acid residue will be deleted, substituted, inserted or added. Such modified DNA can be obtained by conventional methods using treatment with reagents and conditions generating mutations. Such treatment includes treatment the DNA coding for proteins of present invention with hydroxylamine or treatment the bacterium harboring the DNA with UV irradiation or reagent such as N-methyl-N'-nitro-N-nitrosoguanidine or nitrous acid.

The DNA of the present invention includes variants which can be found in the different strains and variants of bacteria belonging to the genus *Escherichia* according to natural diversity. The DNA coding for such variants can be obtained by isolating the DNA, which hybridizes with yddG gene or part of the gene under the stringent conditions, and which codes the protein enhancing L-phenylalanine production. The term "stringent conditions" referred to herein as a condition under which so-called specific hybrid is formed, and non-specific hybrid is not formed. For example, the stringent conditions includes a condition under which DNAs having high homology, for instance DNAs having homology no less than 70% to each other, are hybridized. Alternatively, the stringent conditions are exemplified by conditions which comprise ordinary condition of washing in Southern hybridization, e.g., 60° C., 1×SSC, 0.1% SDS, preferably 0.1×SSC, 0.1% SDS. As a probe for the DNA that codes for variants and hybridizes with yddG gene, a partial sequence of the nucleotide sequence of SEQ ID NO: 1 can also be used. Such a probe may be prepared by PCR using oligonucleotides produced based on the nucleotide sequence of SEQ ID NO: 1 as primers, and a DNA fragment containing the nucleotide sequence of SEQ ID NO: 1 as a template. When a DNA fragment in a length of about 300 bp is used as the probe, the conditions of washing for the hybridization consist of, for example, 50° C., 2×SSC, and 0.1% SDS.

Transformation of bacterium with a DNA coding for a protein means introduction of the DNA into bacterium cell for example by conventional methods to increase expression of the gene coding for the protein of present invention and to enhance the activity of the protein in the bacterial cell.

The methods of the enhancement of gene expression include an increasing of the gene copy number. Introduction of a gene into a vector that is able to function in a bacterium belonging to the genus *Escherichia* increases copy number of the gene. For such purposes multi-copy vectors can be preferably used. The multi-copy vector is exemplified by pBR322, pUC19, pBluescript KS⁺, pACYC177, pACYC184, pAYC32, pMW119, pET22b or the like.

Besides, enhancement of gene expression can be achieved by introduction of multiple copies of the gene into bacterial chromosome by, for example, method of homologous recombination or the like.

In case that expression of two or more genes is enhanced, the genes may be harbored together on the same plasmid or separately on different plasmids. It is also acceptable that one of the genes is harbored on a chromosome, and the other gene is harbored on a plasmid.

On the other hand, the enhancement of gene expression can be achieved by locating the DNA of the present invention under control of more potent promoter instead of the native promoter. Strength of promoter is defined by frequency of acts of the RNA synthesis initiation. Methods for evaluation the strength of promoter and an examples of potent promoters are described by Deuschle, U., Kammerer, W., Gentz, R., Bujard, H. (Promoters in *Escherichia coli*: a hierarchy of in vivo strength indicates alternate structures. EMBO J. 1986, 5, 2987-2994). For example, $P_L$ promoter of lambda phage is known as a potent constitutive promoter. Other known potent promoters are lac promoter, trp promoter, trc promoter, and the like. Using the potent promoter can be combined with multiplication of gene copies.

Methods for preparation of chromosomal DNA, hybridization, PCR, preparation of plasmid DNA, digestion and ligation of DNA, transformation, selection of an oligonucleotide as a primer and the like may be ordinary methods well known to one skilled in the art. These methods are described in Sambrook, J., and Russell D., "Molecular Cloning A Laboratory Manual, Third Edition", Cold Spring Harbor Laboratory Press (2001) and the like.

The bacterium of the present invention can be obtained by introduction of the aforementioned DNAs into bacterium belonging to the genus *Escherichia* inherently having ability to produce L-amino acid. Alternatively, the bacterium of present invention can be obtained by imparting ability to produce L-amino acid to the bacterium belonging to the genus *Escherichia* already harboring the DNAs.

A bacterium belonging to the genus *Escherichia* is not particularly limited so long as it has an ability to produce L-amino acid or it can be conferred the ability. The examples of the bacterium belonging to the genus *Escherichia* include *Escherichia coli*.

As a parent strain which is to be enhanced in activity of the protein of the present invention, the phenylalanine-producing bacterium belonging to the genus *Escherichia* such as the *E. coli* strain AJ12739 (tyrA::Tn10, tyrR) (VKPM B-8197); strain HW1089 (ATCC Accession No. 55371) harboring pheA34 gene (U.S. Pat. No. 5,354,672); mutant MWEC101-b strain (KR8903681); strains NRRL B-12141, NRRL B-12145, NRRL B-12146 and NRRL B-12147 (U.S. Pat. No. 4,407,952) and the like may be used. Also as a parent strain which is to be enhanced in activity of the protein of the present invention, the phenylalanine-producing bacterium belonging to the genus *Escherichia* such as the *E. coli* strain K-12 [W3110 (tyrA)/pPHAB (FERM BP-3566), *E. coil* strain K-12 [W3110 (tyrA)/pPHAD] (FERM BP-12659), *E. coli* K-12 [W3110 (tyrA)/pPHATerm] (FERM BP-12662) and *E. coil* strain K-12 [W3110 (tyrA)/pBR-aroG4,pACMAB] named as AJ 12604 (FERM BP-3579) and the like may be used (European patent EP488424B1).

As a parent strain which is to be enhanced in activity of the protein of the present invention, the tryptophan-producing bacterium belonging to the genus *Escherichia* such as the *E. coli* strains JP4735/pMU3028 (DSM10122) and JP6015/ pMU91 (DSM10123) deficient in the tryptophanyl-tRNA synthetase encoded by mutant trpS gene (U.S. Pat. No. 5,756,345); E. coli strain SV164 (pGH5) having serA allele freed from feedback inhibition by serine (U.S. Pat. No. 6,180,373); E. coli strains AGX17 (pGX44) (NRRL B-12263) and AGX6 (pGX50)aroP (NRRL B-12264) deficient in the enzyme tryptophanase (U.S. Pat. No. 4,371,614); E. coli strain AGX17/pGX50,pACKG4-pps in which a phosphoenolpyruvate-producing ability is enhanced (WO97/08333, U.S. Pat. No. 6,319,696) and the like may be used.

The method of the present invention includes method for producing an L-amino acid, comprising steps of cultivating the bacterium of the present invention in a culture medium, to allow the L-amino acid to be produced and accumulated in the culture medium, and collecting the L-amino acid from the culture medium. Also the method of the present invention includes method for producing L-phenylalanine, comprising steps of cultivating the bacterium of the present invention in a culture medium, to allow L-phenylalanine to be produced and accumulated in the culture medium, and collecting L-phenylalanine from the culture medium. Also the method of the present invention includes method for producing L-tryptophan, comprising steps of cultivating the bacterium of the present invention in a culture medium, to allow L-tryptophan to be produced and accumulated in the culture medium, and collecting L-tryptophan from the culture medium.

In the present invention, the cultivation, the collection and purification of L-amino acids, such as L-phenylalanine and L-tryptophan, from the medium and the like may be performed in a manner similar to the conventional fermentation method wherein an amino acid is produced using a microorganism. A medium used for culture may be either a synthetic medium or a natural medium, so long as the medium includes a carbon source and a nitrogen source and minerals and, if necessary, appropriate amounts of nutrients which the microorganism requires for growth. The carbon source may include various carbohydrates such as glucose and sucrose, and various organic acids. Depending on the mode of assimilation of the used microorganism, alcohol including ethanol and glycerol may be used. As the nitrogen source, various ammonium salts such as ammonia and ammonium sulfate, other nitrogen compounds such as amines, a natural nitrogen source such as peptone, soybean-hydrolysate and digested fermentative microorganism are used. As minerals, potassium monophosphate, magnesium sulfate, sodium chloride, ferrous sulfate, manganese sulfate, calcium chloride, and the like are used. Some additional nutrient can be added to the medium if necessary. For instance, if the microorganism requires tyrosine for growth (tyrosine auxotrophy) the sufficient amount of tyrosine can be added to the medium for cultivation.

The cultivation is performed preferably under aerobic conditions such as a shaking culture, and stirring culture with aeration, at a temperature of 20 to 42° C., preferably 37 to 40° C. The pH of the culture is usually between 5 and 9, preferably between 6.5 and 7.2. The pH of the culture can be adjusted with ammonia, calcium carbonate, various acids, various bases, and buffers. Usually, a 1 to 5-day cultivation leads to the accumulation of the target L-amino acid in the liquid medium.

After cultivation, solids such as cells can be removed from the liquid medium by centrifugation or membrane filtration, and then the target L-amino acid can be collected and purified by conventional method such as ion-exchange, concentration and crystallization methods.

Phenylalanine produced by the method of the present invention may be used for, for example, producing lower alkyl ester of α-L-aspartyl-L-phenylalanine (also referred to as "aspartame"). That is, the method of the present invention includes method for producing lower alkyl ester of α-L-aspartyl-L-phenylalanine by using L-phenylalanine as a raw material. The method comprising synthesizing lower alkyl ester of α-L-aspartyl-L-phenylalanine from L-phenylalanine produced by the method of the present invention as described above and aspartic acid or its derivative. As lower alkyl ester, methyl ester, ethyl ester and propyl ester, or the like can be mentioned.

In the method of the present invention, a process for synthesizing lower alkyl ester of α-L-aspartyl-L-phenylalanine from L-phenylalanine and aspartic acid or its derivative is not particularly limited and any conventional method can be applied so long as L-phenylalanine or its derivative can be used for synthesis of lower alkyl ester of α-L-aspartyl-L-phenylalanine. Concretely, for example, lower alkyl ester of α-L-aspartyl-L-phenylalanine may be produced by the following process (U.S. Pat. No. 3,786,039). L-phenylalanine is esterified to obtain lower alkyl ester of L-phenylalanine. The L-phenylalanine alkyl ester is reacted with L-aspartic acid derivative of which amino group and β-carboxyl group are protected and α-carboxyl group is esterified to activate. The derivative includes N-acyl-L-aspartic anhydride such as N-formyl-, N-carbobenzoxy-, or N-p-methoxycarbobenzoxy-L-aspartic anhydride. By the condensation reaction, mixture of N-acyl-α-L-aspartyl-L-phenylalanine and N-acyl-β-L-aspartyl-L-phenylalanine is obtained. If the condensation reaction is performed under existence of an organic acid of which acid dissociation constant at 37° C. is $10^{-4}$ or less, ratio of α form to β form in the mixture is increased (Japanese Patent Laid-Open Publication No. 51-113841). Then the N-acyl-α-L-aspartyl-L-phenylalanine is separated from the mixture, followed by hydrogenating to obtain α-L-aspartyl-L-phenylalanine.

BEST MODE FOR CARRYING OUT THE INVENTION

Figure 1:
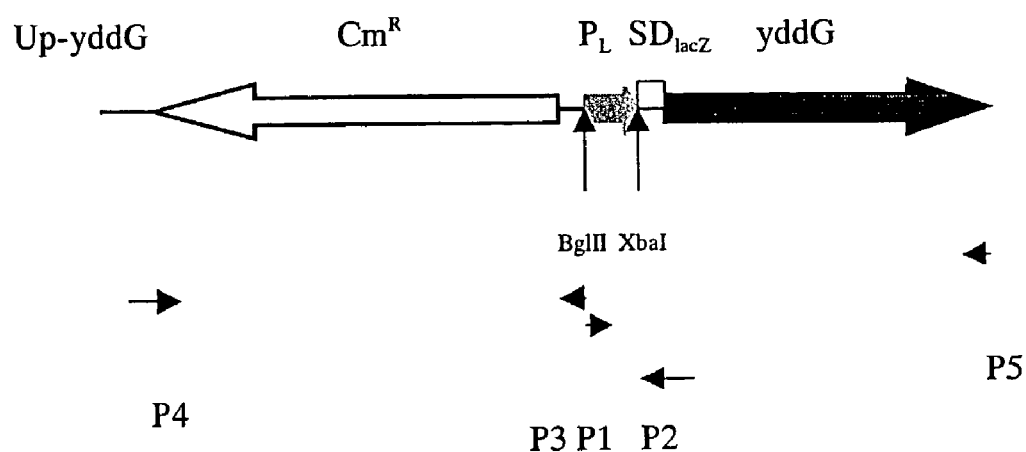
FIG. 1 shows the structure of constructed chromosome region upstream of yddG gene.

The present invention will be more concretely explained below with reference to Examples.

EXAMPLE 1

Cloning the yddG Gene from *E. coli*

The entire nucleotide sequence of *E. coli* strain K-12 has already been determined (Science, 277, 1453-1474, 1997). A PSI-BLAST search revealed that at least 10 rhtA paralogues including yddG gene are present in the genome of *E. coli* K-12. The yddG gene encodes transmembrane protein function of which is unknown.

Based on the reported nucleotide sequence the primers depicted in SEQ ID NO: 3 (primer 1) and NO: 4 (primer 2) were synthesized. The primer 1 is a sequence complementary to a sequence from 91 to 114 bp downstream of the termination codon of yddG gene with a restriction enzyme BamHI recognition site introduced at the 5'-end thereof. The primer 2 is a sequence complementary to a sequence from 224 to 200 bp upstream of the start codon of yddG gene with a restriction enzyme SalI recognition site introduced at the 5'-end thereof.

The chromosomal DNA of E. coli strain TG1 was prepared by an ordinary method. PCR was carried out on "Perkin Elmer GeneAmp PCR System 2400" under the following conditions: 40 sec. at 95° C., 40 sec. at 47° C., 40 sec. at 72° C., 30 cycles by means of Taq polymerase (Fermentas). The obtained PCR fragment containing yddG gene with its own promoter was treated with BamHI and SalI and inserted into multicopy vectors pUC19 and pAYCTER3 previously treated with the same enzymes. Thus, the plasmids pYDDG1 and pYDDG2, respectively, were obtained. The pAYCTER3 vector is a derivative of a pAYC32, a moderate copy number and very stable vector constructed on the basis of plasmid RSF1010 (Christoserdov A. Y., Tsygankov Y. D, Broad-host range vectors derived from a RSF 1010 Tnl plasmid, Plasmid, 1986, v. 16, pp. 161-167). The pAYCTER3 vector was obtained by introduction of the polylinker from pUC19 plasmid and strong terminator rrnB into pAYC32 plasmid instead of its promoter as follows. At first, the polylinker from pUC19 plasmid was obtained by PCR using the primers depicted in SEQ ID NO: 5 and NO: 6. The obtained PCR product was treated with EcoRI and BglII restrictases. The terminator rrnB was also obtained by PCR using the primers depicted in SEQ ID NO: 7 and NO: 8. The obtained PCR product was treated with BglII and BclI restrictases. Then, these two DNA fragments were ligated into pAYC32 plasmid previously treated with EcoRI and BclI restrictases. Thus the pAYCTER3 plasmid was obtained.

EXAMPLE 2

The Effect of the yddG Gene Amplification on the Resistance of E. coli Strain TG1 to the Amino Acid and Amino Acid Analogs The pYDDG1 and pYDDG2 plasmids and the pUC19 and pAYCTER3 vectors were introduced into E. coil strain TG1. Thus the strains TG1 (pYDDG1), TG1 (pYDDG2), TG1 (pUC19) and TG1 (pAYCTER3) were obtained.

Then the ability of these strains to grow in the presence of amino acids and amino acid analogues for each strain were determined on M9 glucose minimal agar plates containing graded concentrations of inhibitor. The plates were spotted with $10^6$ to $10^7$ cells from an overnight culture grown in a minimal medium (supplemented with 100 μg/ml of ampicillin for plasmid strains). The growth was estimated after 44 h incubation at 37° C. The results are presented in Table 1.

TABLE 1

| Substrate | Concentration mg/ml | Growth after 44 h* | | |
|---|---|---|---|---|
| | | TG1 (pUC19)** | TG1 (pYDDG1) | TG1 (pYDDG2) |
| — | — | + | + | + |
| L-phenylalanine | 20.0 | − | + | ± |
| p-fluoro-DL-phenylalanine | 1.0 | − | + | + |
| p-fluoro-DL-phenylalanine | 2.0 | − | + | − |
| 5-fluoro-DL-tryptophane | 0.0005 | − | + | n.d. |

*+: good growth; ±: pour growth; −: no growth; n.d.—not determined.
**The same results were obtained for the TG1 strain harboring pAYCTER3 plasmid.

EXAMPLE 3

Effect of the yddG Gene Amplification on Phenylalanine Production

The phenylalanine-producing E.coli strain AJ12739 was used as a parental strain for transformation with plasmids harboring the yddG gene. The strain AJ12739 has been deposited in the Russian National Collection of Industrial Microorganisms (VKPM) (Russia, 113545 Moscow, 1$^{st}$ Dorozhny proezd, 1) on Nov. 6, 2001 under accession number VKPM B-8197. The original deposit was converted to international deposit according to Budapest Treaty on Aug. 23, 2002.

The phenylalanine-producing strain AJ12739 was transformed with the pYDDG2 plasmid or with the pAYCTER3 vector to obtain the AJ12739/pYDDG2 and AJ12739/pAYCTER3 strains, respectively. These strains were each cultivated at 37° C. for 18 hours in a nutrient broth with 100 mg/l ampicillin, and 0.3 ml of the obtained culture was inoculated into 3 ml of a fermentation medium containing 100 mg/l ampicillin, in a 20×200 mm test tube, and cultivated at 37° C. for 48 hours with a rotary shaker. After the cultivation, the amount of phenylalanine accumulated in the medium was determined by TLC. 10×15 cm TLC plates coated with 0.11 mm layers of Sorbfil silica gel without fluorescent indicator (Stock Company Sorbpolymer, Krasnodar, Russia) were used. Sorbfil plates were developed with a mobile phase: propan-2-ol:ethylacetate:25% aqueous ammonia:water=40:40:7:16 (v/v). A solution (2%) of ninhydrin in acetone was used as a visualizing reagent.

The composition of the fermentation medium (g/l):

| | |
|---|---|
| Glucose | 40.0 |
| $(NH_4)_2SO_4$ | 16.0 |
| $K_2HPO_4$ | 0.1 |
| $MgSO_4 \cdot 7H_2O$ | 1.0 |
| $FeSO_4 \cdot 7H_2O$ | 0.01 |
| $MnSO_4 \cdot 5H_2O$ | 0.01 |
| Thiamine-HCl | 0.0002 |
| Yeast extract | 2.0 |
| Tyrosine | 0.125 |
| $CaCO_3$ | 20.0 |

Glucose and magnesium sulfate are sterilized separately. $CaCO_3$ dry-heat sterilized at 180° for 2 h. pH is adjusted to 7.0. Antibiotic is introduced into the medium after sterilization. The results are presented in Table 2.

TABLE 2

| E. coli strain | $OD_{600}$ | Amount of phenylalanine, g/l |
|---|---|---|
| AJ12739 (pAYCTER3) | 7.0 | 1.5 |
| AJ12739 (pYDDG2) | 7.8 | 1.9 |

It can be seen from the Table 2 that the yddG gene amplification improved phenylalanine productivity of the AJ12739 strain.

EXAMPLE 4

Substitution of the Native Upstream Region of yddG Gene by the Hybrid Regulatory Element Carrying the $P_L$ Promoter and $SD_{lacZ}$ in E. coli Chromosome To enhance yddG gene expression, the early $P_L$ promoter region of phage λ (Giladi et al., J.Mol.Biol., 260, 484-491, 1996) linked to the Shine-Dalgarno sequence (SD sequence) of the lacZ gene from E. coli was integrated upstream yddG coding region in the chromosome of the E. coli strain BW25113 instead of the native region by method described by Datsenko K. A., and Wanner B. L. (Proc.Natl.Acad.Sci.USA,97,6640-6645,2000) also called as a "Red-driven integration". In addition, the artificial DNA fragment carried chloramphenicol resistance gene ($Cm^R$) (FIG. 1). Nucleotide sequence of the substituted native region located upstream of yddG gene is presented in the Sequence listing (SEQ ID NO: 9)

Construction of the abovementioned artificial DNA fragment integrated into the corresponding region of bacterial chromosome was fulfilled in the several steps. At the first step, the DNA fragment carried the BglII-restriction site in the "upstream" region, $P_L$ promoter and the SD sequence of lacZ gene from E. coli linked directly to the ATG-initiating codon of yddG gene in the "downstream" region was obtained by PCR. λ DNA (#SD0011, "Fermentas", Lithuania) was used for the PCR as a template. PCR was provided using primers P1 (SEQ ID NO: 10) and P2 (SEQ ID NO: 11). Primer P1 contains BglII-restriction site. Primer P2 contains lambda DNA sequence, XbaI restriction site, SD sequence of lacZ gene from E. coli and 36 nucleotides from yddG reading frame. The sequence from yddG gene was introduced into primer P2 for further Red-driven integration of the fragment into the bacterial chromosome.

In all cases PCR was provided using the amplificatory "Perkin-Elmer 2400 GeneAmp PCR System". The reaction mixture with the total volume of 100 µl consists of: 10 µl of 10× PCR-buffer ("Fermentas", Lithuania) with addition of $MgCl_2$ up to the final concentration—2 mM in the reaction mixture, 200 µM each of dNTP, 400 nM each of the exploited primers and 2 u Taq-polymerase ("Fermentas", Lithuania). The quantity of the template DNA for the further PCR-driven amplification has been added in the reaction mixture in calculation of 0.2 ng of the target DNA fragment. The temperature PCR condition were following: initial DNA denaturation for 5 min at 95° C. followed by 30 cycles of denaturation at +95° C. for 30 sec, annealing at +50° C. for 30 sec, elongation at +72° C. for 30 sec and the final polymerization for 5 min at +72° C.

In the parallel, the second stage of construction of the DNA fragment of interest has been provided. $Cm^R$ gene was amplified by PCR using the commercially available plasmid pACYC184 (GenBank/EMBL accession number X06403, "Fermentas", Lithuania) as the template and primers P3 (SEQ ID NO: 12) and P4 (SEQ ID NO: 13). Primer P3 contains the BglII-restriction site used for further joining with the earlier obtained DNA fragment carried $P_L$ promoter. Promoter P4 contains 36 nucleotides located upstream of yddG gene from E. coli necessary for further Red-driven integration of the fragment into the bacterial chromosome.

Two obtained DNA fragments was treated with BglII restriction endonuclease followed by ligation procedure using T4 DNA ligase (Maniatis T., Fritsch E. F., Sambrook, J.: Molecular Cloning:A Laboratory Manual. $3^{rd}$ edn. Cold Spring Harbor, N.Y.: Cold Spring Harbor Laboratory Press, 2001).

The ligated product was amplified by PCR using primers P2 and P4. PCR was provided as described above with the following exceptions: the reaction mixture contained 2 ng of ligated products and elongation time was increased up to 2 min. The structure of constructed DNA region upstream yddG gene is shown on FIG. 1. Nucleotide sequence of the constructed DNA region is presented in SEQ ID NO: 14.

The obtained DNA fragment purified by precipitation with ethanol was used for electroporation and Red-driven integration into the bacterial chromosome of the E. coli strain BW25113. The recombinant plasmid pKD46 (Datsenko, K. A., Wanner, B. L., Proc.Natl.Acad.Sci.USA, 97, 6640-6645, 2000) with the thermosensitive replicon was used as the donor of the phage λ-derived genes responsible for the Red-driven recombination system.

The cells of BW25113 (pKD46) were grown overnight at +30° C. in the liquid LB-medium with addition of ampicillin (100 µg/ml), then diluted 1:100 by the SOC-medium (Yeast extract, 5 g/l; NaCl, 0.5 g/l; Tryptone, 20 g/l; KCl, 2.5 mM; $MgCl_2$, 10 mM) with addition of ampicillin (100 µg/ml) and L-arabinose (10 mM) (arabinose is used for inducing the plasmid encoding genes of Red-driven system) and grown at +30° C. to reach the optical density of the bacterial culture $OD_{600}$=0.4-0.7. The grown cells from 10 ml of the bacterial culture were washed 3 times by the ice-cold de-ionized water followed by suspending in 100 µl of the water. 10 µl of DNA fragment (10 ng) solved in the de-ionized water has been added to the cell suspension. The electroporation was performed by "Bio-Rad" electroporator (USA) (No. 165-2098, version 2-89) according to the manufacturer's instructions. Shocked cells were added to 1 -ml SOC, incubated 2 h at 37° C., and then were spreaded onto L-agar containing 25 µg/ml of chloramphenicol. Colonies grown within 24 h were tested for the presence of $Cm^R$ marker upstream of yddG gene by PCR using primers P4 (SEQ ID NO: 13) and P5 (SEQ ID NO: 15). For this purpose, a freshly isolated colony was suspended in 20 µl water and then 1 µl was used in PCR. PCR conditions are following: initial DNA denaturation for 10 min at 95° C.; then 30 cycles of denaturation at +95° C. for 30 sec, annealing at +50° C. for 30 sec and elongation at +72° C. for 50 sec; the final polymerization for 5 min at +72° C. A few $Cm^R$ colonies tested contained necessary 2172 nt DNA fragment.

EXAMPLE 5

Effect of Enhanced yddG Gene Expression on Tryptophan Production

The tryptophan-producing E.coli strain SV164 (pGH5) was used as a parental strain for evaluation of effect of enhanced yddG gene expression on tryptophan production. The strain SV164 (pGH5) is described in details in U.S. Pat. No. 6,180,373 or European patent 0662143.

To test an effect of enhancement of yddG gene expression under control of strong constitute promoter $P_L$ on tryptophan production, the abovementioned DNA fragment from the chromosome of E. coli strain BW25113 was transferred to tryptophan-producing E.coli strain SV164 (pGH5) by P1 transduction (Miller, J. H. (1972) Experiments in Molecular Genetics, Cold Spring Harbor Lab. Press, Plainview, N.Y.) to obtain SV164 $P_L$-yddG (pGH5).

Both SV164 (pGH5) and SV164 $P_L$-yddG (pGH5) strains were cultivated with shaking at 37° C. for 18 hours in a 3 ml of nutrient broth supplemented with 20 µg/ml of tetracycline (marker of pGH5 plasmid). 0.3 ml of the obtained cultures were inoculated into 3 ml of a fermentation medium containing tetracycline (20 µg/ml) in 20×200 mm test tubes, and cultivated at 37° C. for 48 hours with a rotary shaker at 250 rpm.

The composition of the fermentation medium is presented in Table 3.

TABLE 3

| Sections | Component | Final concentration, g/l |
|---|---|---|
| A | KH$_2$PO$_4$ | 1.5 |
|   | NaCl | 0.5 |
|   | (NH$_4$)$_2$SO$_4$ | 1.5 |
|   | L-Methionine | 0.05 |
|   | L-Phenylalanine | 0.1 |
|   | L-Tyrosine | 0.1 |
|   | Mameno (total N) | 0.07 |
| B | Glucose | 40.0 |
|   | MgSO$_4$•7H$_2$O | 0.3 |
| C | CaCl$_2$ | 0.011 |
| D | FeSO$_4$ x 7H$_2$O | 0.075 |
|   | Sodium citrate | 1.0 |
| E | Na$_2$MoO$_4$•2H$_2$O | 0.00015 |
|   | H$_3$BO$_3$ | 0.0025 |
|   | CoCl$_2$•6H$_2$O | 0.00007 |
|   | CuSO$_4$•5H$_2$O | 0.00025 |
|   | MnCl$_2$•4H$_2$O | 0.0016 |
|   | ZnSO$_4$•7H$_2$O | 0.0003 |

TABLE 3-continued

| Sections | Component | Final concentration, g/l |
|---|---|---|
| F | Thiamine-HCl | 0.005 |
| G | CaCO$_3$ | 30.0 |
| H | Pyridoxine | 0.03 |

Section A had pH 7.1 adjusted by NH$_4$OH. Each section was sterilized separately.

After the cultivation, the amount of tryptophan accumulated in the medium was determined by TLC as described in Example 3. Obtained data are presented in the Table 4.

TABLE 4

| E. coli strain | OD$_{600}$* | Amount of tryptophan, g/l* |
|---|---|---|
| SV164 (pGH5) | 7.0 | 3.72 ± 0.13 |
| SV164 P$_L$-yddG (pGH5) | 7.0 | 4.17 ± 0.35 |

*There are presented results of at least six independent experiments for each strain.

It can be seen from the Table 4 that the enhancement of yddG gene expression improved tryptophan productivity of the SV164 (pGH5) strain.

What is claimed is:

1. A recombinant *Escherichia coli* bacterium that has the ability to produce and accumulate an aromatic L-amino acid, wherein the aromatic L-amino acid production by said bacterium is enhanced by enhancing activity of a protein in a cell of said bacterium beyond the levels observed in a wild-type of said bacterium, wherein said protein is as defined in the following (A), (B), or (C):

(A) a protein which consists of the amino acid sequence of SEQ ID NO: 2;
  (B) a protein which consists of the amino acid sequence of SEQ ID NO: 2 except wherein one to five amino acids are deleted, substituted, inserted, or added; or
  (C) a protein which consists of the amino acid sequence that is encoded by a nucleotide sequence that hybridizes with the complement of the nucleotide sequence of SEQ ID NO: 1 under stringent conditions comprising 60° C., 1×SSC, 0.1% SDS;

wherein said protein defined in (A), (B), or (C) has an activity to make said bacterium resistant to L-phenylalanine, fluoro-phenylalanine or 5-fluoro-DL-tryptophan and wherein the activity of said protein defined in (A), (B), or (C) is enhanced by:
  a) transformation of said bacterium with a DNA encoding said protein and expressing the protein in said bacterium,
  b) replacing the native promoter that precedes the DNA encoding said protein on the chromosome of the bacterium with a more potent promoter, or
  c) introduction of multiple copies of the DNA encoding said protein into the chromosome of said bacterium and expressing the protein in said bacterium.

2. The bacterium according to claim 1, wherein the transformation is performed with a multicopy vector containing said DNA.

3. The bacterium according to claim 1, wherein said more potent promoter is selected from the group consisting of a $P_1$, promoter of lambda phage, a lac promoter, a trp promoter, and a trc promoter.

4. A method for producing an aromatic L-amino acid, which comprises cultivating the bacterium of claims 1, 2, or 3 in a culture medium and collecting from the culture medium the aromatic L-amino acid.

5. The method according to claim 4, wherein the aromatic L-amino acid is L-phenylalanine.

6. The method according to claim 5, wherein the bacterium has enhanced expression of genes for phenylalanine biosynthesis as compared to a wild-type of said bacterium.

7. The method according to claim 4, wherein the aromatic L-amino acid is L-tryptophan.

8. The method according to claim 7, wherein the bacterium has enhanced expression of genes for tryptophan biosynthesis as compared to a wild-type of said bacterium.

9. A recombinant *Escherichia coli* bacterium, which has the ability to accumulate aromatic L-amino acid in a medium, wherein the aromatic L-amino acid production by said bacterium is enhanced by enhancing activity of a protein in a cell of said bacterium beyond the levels observed in a wild-type of said bacterium, and in which said protein consists of the amino acid sequence of SEQ ID NO: 2 and said protein has the activity to make the bacterium resistant to L-phenylalanine, fluoro-phenylalanine or 5fluoro-DL-tryptophan, wherein the activity of the protein is enhanced by transformation of the bacterium with a DNA encoding the protein to express the protein in the bacterium, by replacing the native promoter which precedes the DNA on the chromosome of the bacterium with a more potent promoter, or by introduction of multiple copies of the DNA encoding said protein into the chromosome of said bacterium to express the protein in said bacterium.

10. The bacterium according to claim 9, wherein said activity of the protein is to make the bacterium resistant to fluoro-phenylalanine or 5-fluoro-DL-tryptophan.

11. The bacterium according to claim 9, wherein the aromatic L-amino acid is L-phenylalanine or L-tryptophan.

12. The bacterium according to claim 9, wherein said activity of the protein is to make the bacterium resistant to L-phenylalanine.

13. The bacterium according to claim 9, wherein the transformation is performed with a multicopy vector containing said DNA.

14. The bacterium according to claim 9, wherein the protein is encoded by the nucleotide sequence of SEQ ID NO: 1.

15. A recombinant *Escherichia coli* bacterium, which has the ability to accumulate aromatic L-amino acid in a medium, wherein the aromatic L-amino acid production by said bacterium is enhanced by enhancing activity of a protein in a cell of said bacterium beyond the levels observed in a wild-type of said bacterium, and in which said protein is encoded by the nucleotide sequence which hybridizes with the complement of the nucleotide sequence of SEQ ID NO: 1 under stringent conditions comprising 60° C., 1×SSC, 0.1% SDS and said protein has the activity to make the bacterium resistant to L-phenylalanine, fluoro-phenylalanine or 5fluoro-DL-tryptophan, wherein the activity of the protein is enhanced by transformation of the bacterium with a DNA encoding the protein to express the protein in the bacterium, by replacing the native promoter which precedes the DNA on the chromosome of the bacterium with a more potent promoter, or by introduction of multiple copies of the DNA encoding said protein into the chromosome of said bacterium to express the protein in said bacterium.

16. The bacterium according to claim 15, wherein said activity of the protein is to make the bacterium resistant to fluoro-phenylalanine or 5-fluoro-DL-tryptophan.

17. The bacterium according to claim 15, wherein the aromatic L-amino acid is L-phenylalanine or L-tryptophan.

18. The bacterium according to claim 15, wherein said activity of the protein is to make the bacterium resistant to L-phenylalanine.

19. The bacterium according to claim 15, wherein the transformation is performed with a multicopy vector containing said DNA.

20. A method for producing an aromatic L-amino acid, which comprises cultivating the bacterium according to any one of claims 9-12, 13, 14, 15-18, or 19.

21. A recombinant *Escherichia coli* bacterium, which has the ability to accumulate aromatic L-amino acid in a medium, wherein the aromatic L-amino acid production by said bacterium is enhanced by enhancing activity of a protein in a cell of said bacterium beyond the levels observed in a wild-type of said bacterium, and in which said protein consists of the amino acid sequence of SEQ ID NO: 2 except wherein one to five amino acids are deleted, substituted, inserted, or added and said protein has the activity to make the bacterium resistant to L-phenylalanine, fluoro-phenylalanine or 5fluoro-DL-tryptophan, wherein the activity of the protein is enhanced by transformation of the bacterium with a DNA encoding the protein to express the protein in the bacterium, by replacing the native promoter which precedes the DNA on the chromosome of the bacterium with a more potent promoter, or by introduction of multiple copies of the DNA encoding said protein into the chromosome of said bacterium to express the protein in said bacterium.

22. The bacterium according to claim 21, wherein said activity of the protein is to make the bacterium resistant to fluoro-phenylalanine or 5-fluoro-DL-tryptophan.

23. The bacterium according to claim 21, wherein said activity of the protein is to make the bacterium resistant to L-phenylalanine.

24. The bacterium according to claim 21, wherein the aromatic L-amino acid is L-phenylalanine or L-tryptophan.

25. The bacterium according claim 21, wherein the transformation is performed with a multicopy vector containing said DNA.

26. A method for producing an aromatic L-amino acid, which comprises cultivating the bacterium according to any one of claims 21-24 or 25.

* * * * *

UNITED STATES PATENT AND TRADEMARK OFFICE
CERTIFICATE OF CORRECTION

| | | |
|---|---|---|
| PATENT NO. | : 7,666,655 B2 | Page 1 of 1 |
| APPLICATION NO. | : 10/302997 | |
| DATED | : February 23, 2010 | |
| INVENTOR(S) | : Vitushkina et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 417 days.

Signed and Sealed this

Seventh Day of December, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,666,655 B2 | Page 1 of 1 |
| APPLICATION NO. | : 10/302997 | |
| DATED | : February 23, 2010 | |
| INVENTOR(S) | : Sergei V. Mashko et al. | |

It is certified that error appears in the above-identified patent and that said Letters Patent is hereby corrected as shown below:

Please change the following:

In column 22, line 32, "$P_1$" should read -- $P_1.$ --.

In column 22, line 59, "5fluoro" should read -- 5-fluoro --

In column 23, line 24, "5fluoro" should read -- 5-fluoro --

In column 24, line 16, "5fluoro" should read -- 5-fluoro --

Signed and Sealed this
Nineteenth Day of April, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,666,655 B2 | Page 1 of 1 |
| APPLICATION NO. | : 10/302997 | |
| DATED | : February 23, 2010 | |
| INVENTOR(S) | : Sergei V. Mashko et al. | |

It is certified that error appears in the above-identified patent and that said Letters Patent is hereby corrected as shown below:

Please change the following:

In column 22, line 32, "$P_1$" should read -- $P_L$ --.

In column 22, line 59, "5fluoro" should read -- 5-fluoro --

In column 23, line 24, "5fluoro" should read -- 5-fluoro --

In column 24, line 16, "5fluoro" should read -- 5-fluoro --

This certificate supersedes the Certificate of Correction issued April 19, 2011.

Signed and Sealed this
Twenty-sixth Day of July, 2011

David J. Kappos
*Director of the United States Patent and Trademark Office*